(12) United States Patent
Sobolewski

(10) Patent No.: US 8,467,979 B2
(45) Date of Patent: Jun. 18, 2013

(54) INTELLIGENT SPORT SHOE SYSTEM

(75) Inventor: Zbigniew S. Sobolewski, Monument, CO (US)

(73) Assignee: Alluvial Joules, Inc., Dalton, GA (US)

( * ) Notice: Subject to any disclaimer, the term of this patent is extended or adjusted under 35 U.S.C. 154(b) by 354 days.

(21) Appl. No.: 12/901,465

(22) Filed: Oct. 8, 2010

(65) Prior Publication Data
US 2011/0087445 A1   Apr. 14, 2011

Related U.S. Application Data

(60) Provisional application No. 61/249,965, filed on Oct. 8, 2009.

(51) Int. Cl.
*G06F 19/00* (2011.01)

(52) U.S. Cl.
USPC ............ 702/44; 702/141; 702/182; 702/144; 702/176; 702/160; 600/587; 600/595; 600/592; 36/25 R; 73/862.391

(58) Field of Classification Search
USPC .... 702/44, 141, 182, 144, 176, 160; 600/587, 600/595, 592, 485; 36/114, 136, 25 R, 103, 36/29, 30 R
See application file for complete search history.

(56) References Cited

U.S. PATENT DOCUMENTS

| | | | |
|---|---|---|---|
| 5,373,651 A | | 12/1994 | Wood |
| 6,018,705 A * | | 1/2000 | Gaudet et al. ................. 702/176 |
| 6,052,654 A * | | 4/2000 | Gaudet et al. ................. 702/160 |
| 6,611,789 B1 * | | 8/2003 | Darley ........................... 702/160 |
| 6,876,947 B1 * | | 4/2005 | Darley et al. .................. 702/160 |
| 6,898,550 B1 * | | 5/2005 | Blackadar et al. ............ 702/182 |
| 7,072,789 B2 * | | 7/2006 | Vock et al. ..................... 702/141 |
| 7,200,517 B2 * | | 4/2007 | Darley et al. .................. 702/160 |
| 7,353,137 B2 | | 4/2008 | Vock et al. |
| 7,428,471 B2 * | | 9/2008 | Darley et al. .................. 702/182 |
| 7,428,472 B2 * | | 9/2008 | Darley et al. .................. 702/182 |
| 7,470,234 B1 | | 12/2008 | Elhag et al. |
| 7,503,133 B2 * | | 3/2009 | Muraoka ......................... 36/131 |
| 7,607,243 B2 | | 10/2009 | Berner, Jr. et al. |
| 7,617,071 B2 * | | 11/2009 | Darley et al. .................. 702/165 |

(Continued)

OTHER PUBLICATIONS

Wertsch et al., A Portable Insole Plantar Pressure Measurement System, Journal of Rehabilitation Research and Development, vol. 29, No. 1, Winter 1992, pp. 13-18.

(Continued)

*Primary Examiner* — Carol Tsai
(74) *Attorney, Agent, or Firm* — Christopher J. Kulish

(57) ABSTRACT

The present invention is directed to a system for providing information to an athlete concerning the efficiency with which the athlete is using energy in moving relative to the ground or some other surface. In one embodiment, the system includes a plurality of pressure sensors that are associated with a shoe and generate pressure related data. The system further includes a processing system that processes the pressure data produced by the sensors to determine energy efficiency related information and make this information available to the wearer of the shoe so that the wearer can, if needed or desired, takes steps to improve their energy efficiency.

11 Claims, 4 Drawing Sheets

U.S. PATENT DOCUMENTS

| | | | |
|---|---|---|---|
| 7,631,382 B2 * | 12/2009 | DiBenedetto et al. | 12/142 P |
| 7,698,101 B2 | 4/2010 | Alten et al. | |
| 7,771,371 B2 | 8/2010 | Avni | |
| 8,056,268 B2 * | 11/2011 | DiBenedetto et al. | 36/132 |
| 8,122,773 B2 * | 2/2012 | Wyatt et al. | 73/818 |
| 8,280,681 B2 * | 10/2012 | Vock et al. | 702/173 |
| 2006/0248965 A1 * | 11/2006 | Wyatt et al. | 73/862.391 |
| 2007/0203533 A1 * | 8/2007 | Goren et al. | 607/49 |
| 2007/0250286 A1 * | 10/2007 | Duncan et al. | 702/139 |
| 2008/0167580 A1 * | 7/2008 | Avni et al. | 600/587 |
| 2008/0243265 A1 * | 10/2008 | Lanier et al. | 623/24 |
| 2009/0235739 A1 | 9/2009 | Morris Bamberg et al. | |
| 2009/0240171 A1 | 9/2009 | Morris Bamberg et al. | |
| 2009/0308179 A1 * | 12/2009 | Wyatt et al. | 73/862.391 |
| 2010/0152619 A1 * | 6/2010 | Kalpaxis et al. | 600/592 |
| 2011/0054359 A1 * | 3/2011 | Sazonov et al. | 600/595 |

OTHER PUBLICATIONS

Morris et al., Shoe-Integrated Sensor System for Wireless Gait Analysis and Real-Time Feedback, Proceedings fo the Second Joint EMBS/BMES Conference, Oct. 23-26, 2002, pp. 2468-2469.

Hessert et al., Foot Pressure Distribution During Walking in Young and Old Adults, BMC Geriatrics, May 19, 2005.

Chumanov et al., Tracking the Position of Insole Pressure Sensors During Walking and Running, date of publication unknown.

Alango Ltd., Gait Research System User's Manual, Apr. 7, 2004 (date of publication unknown).

* cited by examiner

INTELLIGENT SPORT SHOE SYSTEM

CROSS-REFERENCE TO RELATED APPLICATIONS

This application claims the benefit of U.S. provisional patent application No. 61/249,965 entitled "Intelligent Dynamic Data Collection system For Measurement of Power Output and Energy Exhausted During Exercise or Training" and filed on Oct. 8, 2009, which application is incorporated by reference into this application in its entirety.

FIELD OF THE INVENTION

The present invention relates to a sport shoe capable of producing data relating to the interaction of the athlete wearing the shoe with their environment and the analysis of the data to produce information indicative of athletic performance.

BACKGROUND OF THE INVENTION

Shoes that incorporate one or more sensors to measure some physical parameter related to the interaction of the wearer of the shoe with their environment and the analysis of the data produced by the sensor(s) generally fall into two applications. The first application is in providing health related information. For instance, there are shoes with sensors that provide data that can be used to analyze asymmetry in the gait of individuals that can lead to arthritic conditions. Apparently, individuals with unilateral lower limb amputations have a tendency to favor the leg with the prosthetic and overload the non-amputated leg. This apparently can lead to osteoarthritis in the non-amputated leg. The data produced by shoes with sensors that are worn by these individuals apparently can be used to provide feedback to the individual that non-amputated leg is being overloaded. The individual can then take corrective action. In another health related application, shoes with sensors are used to provide feedback to children that are exhibiting a pattern physical inactivity that can lead to significant health related issues later in life. The feedback provided by these children is intended to help or aide such children in breaking this pattern.

The second application of shoes that incorporate sensors is in producing sport performance related information. In this application, shoes with sensors are used to provide detailed information concerning the motion of the shoe and the force of pressure profile that is applied to the shoe during a particular sporting activity. Additionally, such shoes are used to provide data that can be analyzed to determine the amount of energy expended during a sporting activity.

SUMMARY OF THE INVENTION

The present invention is directed to shoes with sensors that provide data that is analyzed to provide sport performance related feedback. More specifically, the invention is directed to a system that includes a shoe with sensors that provide pressure data that is analyzed to provide the wearer of the shoe feedback information concerning their energy efficiency. In the case of an individual that is running, the calculated energy efficiency is indicative of how well they are using the energy being generated to propel themselves forward in a run. To elaborate, when an individual is running, each foot goes through a cycle that involves two phases. In the first phase, the foot is in contact with the ground. Characteristic of the second phase is that the foot is no longer in contact with the ground. The first phase can be broken down into two sub-phases. Namely, a landing sub-phase and a launching sub-phase. During the landing sub-phase, the runner is losing energy relative to moving the runner forward. This can be viewed as energy that is attenuating the forward movement of the runner or energy is being imparted from the runner into the surface over which the runner is traveling. In contrast, during the launching sub-phase, the runner is delivering energy relative to moving the runner forward. The energy efficiency that is calculated for a single occurrence of the first phase of the runner's foot being in contact with the ground is the difference between the energy delivered during the launching sub-phase of one step and the energy lost during landing sub-phase of the subsequent step divided by the energy delivered during the launching sub-phase. This energy efficiency can, in turn, be analyzed by the runner or their coach to make changes in the runner's mechanics to improve the efficiency and, in all likelihood, reduce race times.

DETAILED DESCRIPTION

Figure 1:
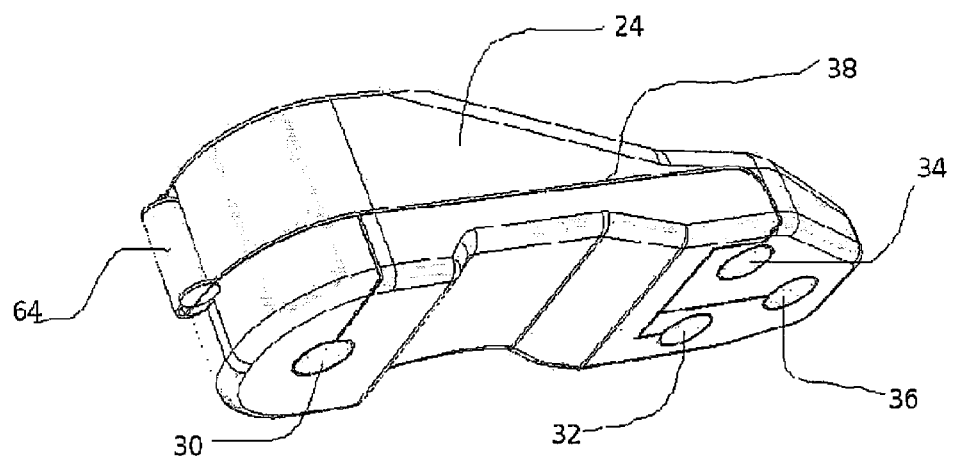
FIG. 1 illustrates an embodiment of an athletic shoe that incorporates a plurality of pressure sensors and a data processing unit for receiving data from the sensors.
Figure 2:
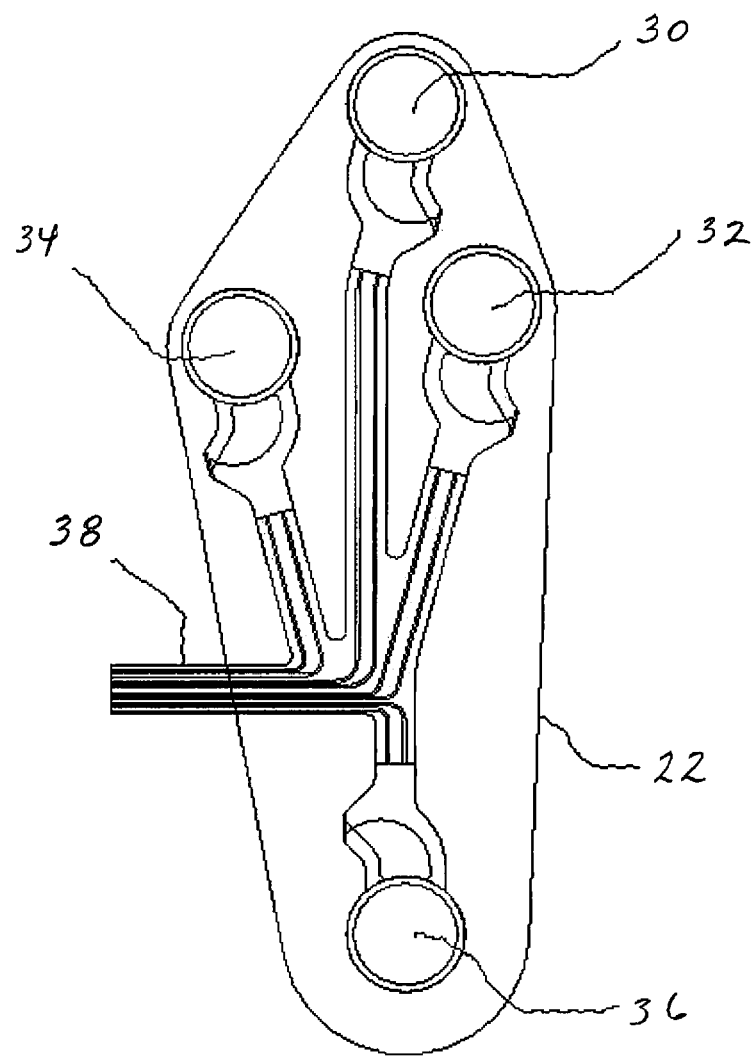
FIG. 2 provides a detailed view of the pressure sensors incorporated into the shoe shown in FIG. 1 and the flex circuit that connects the sensors to the data processing unit.
Figure 3:
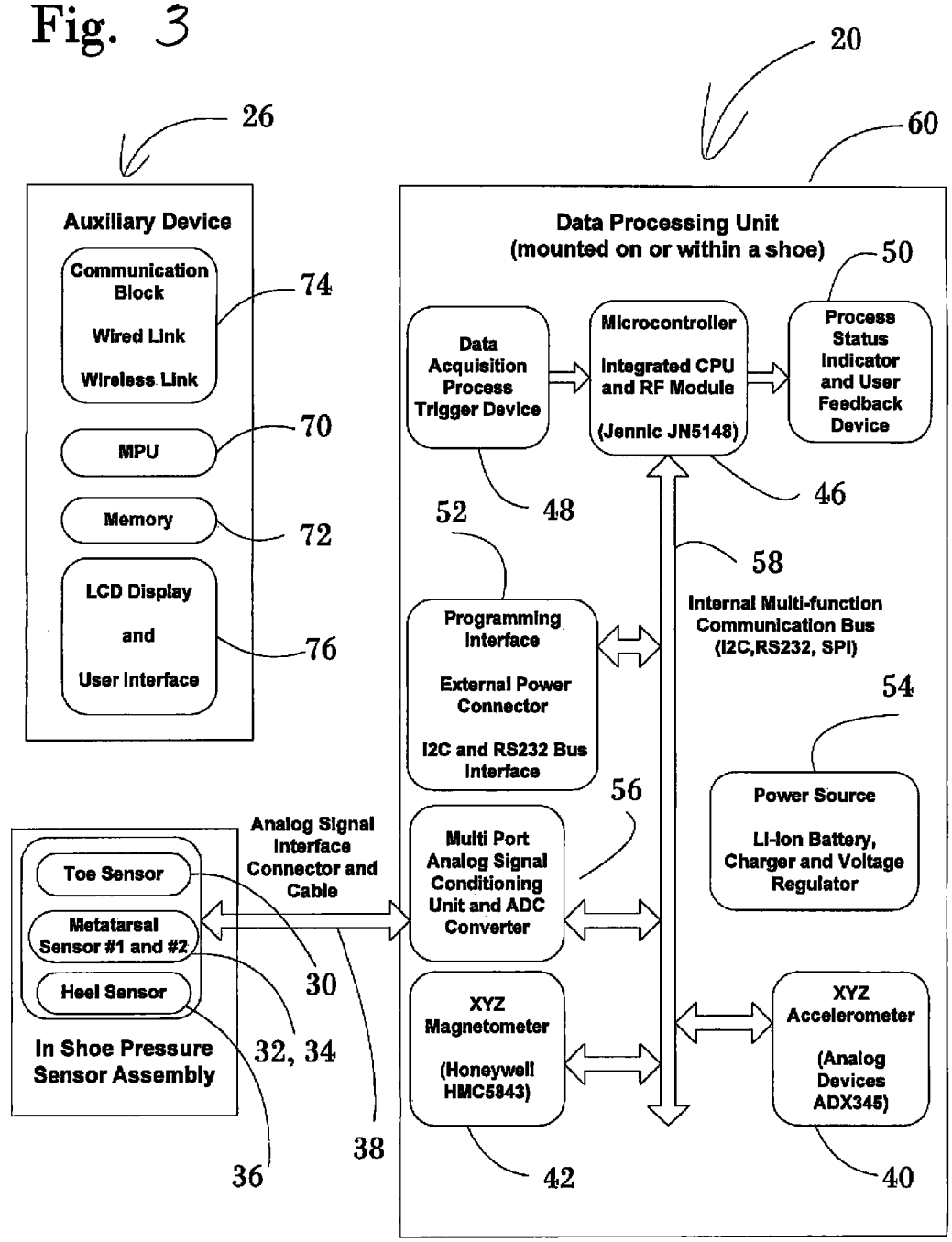
FIG. 3 is a block diagram of an embodiment of the system of the present invention.

With reference to FIGS. 1-4, an embodiment of a system that acquires data relating to the interaction between a wearer's shoe and the ground or other surface relative to which the individual is moving, analyzes the data, and provides the individual with energy efficiency information, which is hereinafter referred to as apparatus 20, is described. The system 20 is comprised of: (a) a shoe 22, (b) a data acquisition and processing system 24 that is operatively attached to the shoe 22; and (c) an auxiliary device 26 that is capable of communicating with the system 24, analyzing data and/or information provided by the system 24, and providing the wearer with feedback concerning their energy efficiency with respect to whatever movement is causing the shoe to interact with the ground or other surface.

The shoe 22 can be in whatever form is suitable for the particular athletic endeavor in which the wearer is engaged. The only requirement of the shoe 22 from the perspective of the operation of the apparatus 20 is that the shoe 22 needs to be able to accommodate the data acquisition and processing system 24.

Generally, the data acquisition and processing system 24 is comprised of a plurality of sensors for generating data relating to the interaction between the shoe 22 and the ground or other surface relative to which the wearer is moving the shoe 22 and a processor for processing the data generated by the sensors, providing data that has been processed to the auxiliary device 26, and providing an interface to the wearer that allows the wearer to interact with the system 24.

The plurality of sensors includes a heel pressure sensor 30, a medial-metatarsal pressure sensor 32, a lateral-metatarsal pressure sensor 34, and a toe pressure sensor 36 that each operate to generate an analog signal that is indicative of the pressure being exerted by the wearer at the location of the sensor. In the illustrated embodiment, the heel pressure sensor 30, medial-metatarsal pressure sensor 32, lateral-metatarsal pressure sensor 34, and toe pressure sensor 36 are each similar to Tekscan FlexiForce® sensors. A flex circuit 38 connects these pressure sensors to the processor. An alternative to the use of a flex circuit are individual wires. The pressure sensors 30, 32, 34, and 36 are located such that when the wearer is wearing the shoe, the sensors are disposed between the bottom of the wearer's foot and the ground or other surface over which the wearer is moving. In one embodiment, the pressures sensors 30, 32, 34, and 36 are integrated into a removable insole. In another embodiment, the sensors 30, 32, 34, and 36 are embedded within the sole of the shoe 22. While the pressure sensors 30, 32, 34, and 36 are shown as being identical and have a circular foot print, it should be appreciated that pressure sensors do not need to be identical to one another, can be of different size, and can be of different shape.

The plurality of sensors also includes a three-axis accelerometer 40 and a three-axis magnetometer 42. In the illustrated embodiment, the accelerometer 40 is an Analog Devices ADX345 digital accelerometer that operates to provide a 10-13 bit digital signal to an I2C serial bus interface for transfer to the microcontroller. In the illustrated embodiment, the magnetometer 42 is a Honeywell HMC5843 digital compass that operates to provide a 12-bit digital signal to an I2C serial bus interface for transfer to the microcontroller.

The processor is comprised of a microcontroller with wireless communication capability 46 (hereinafter "microcontroller 46"), trigger 48, output device 50, interface 52, a power source 54, an analog conditioning and analog-to-digital converter circuit 56, and multi-function bus 58. Generally, the wireless microcontroller 46 operates to: (a) control the operation of the heel pressure sensor 30, medial-metatarsal pressure sensor 32, lateral-metatarsal pressure sensor 34, toe pressure sensor 36, three-axis accelerometer 40, and three-axis magnetometer 42, (b) process the data produced by the heel pressure sensor 30, medial-metatarsal pressure sensor 32, lateral-metatarsal pressure sensor 34, toe pressure sensor 36, three-axis accelerometer 40, and three-axis magnetometer 42, and (c) wirelessly communicate processed data produced by the heel pressure sensor 30, medial-metatarsal pressure sensor 32, lateral-metatarsal pressure sensor 34, toe pressure sensor 36, three-axis accelerometer 40, and three-axis magnetometer to the auxiliary device 26. In the illustrated embodiment, the wireless microcontroller 46 is a Jennie JN5148 that includes a transceiver that operates at 2.4 GHz pursuant to the IEEE 802.15.4 specification and conducts communications in accordance with the ZigBee specification. Other wireless microcontrollers and combinations of elements that provide comparable functionality known to those in the art can also be utilized.

The trigger 48 provides the user with the ability to inform the microprocessor 46 that the wearer either wants to initiate the taking of data by the sensors or terminate the taking of data by the sensors. The output device 50 is utilized by the microprocessor 46 to provide the wearer with status information (e.g., whether the sensors have been activated or deactivated) and feedback on the wearer's manipulation/use of the apparatus.

The interface 52 provides the wearer and others with wired access to the microcontroller 46 and other elements of the apparatus that are connected to the multi-function bus 58. In addition, the interface 52 provides an interface for recharging the power source 54.

The power source 54 includes a battery and related charging and regulator circuitry. The battery provides power to the other elements of the processor and to the accelerometer 40 and magnetometer 42 by a power bus, direct wiring, or combination thereof. In the illustrated embodiment, the battery is a lithium-ion battery.

The analog conditioning and analog-to-digital converter circuit 56 (hereinafter "sensor interface circuitry 56") provides a path for communications between the pressure sensors in the shoe 22 and the microcontroller 46 and converts any analog data produced by the pressure sensors into digital data suitable for communication to the microcontroller over the multi-function bus 58. The multi-function bus 58 allows the microcontroller 46 to communicate with the accelerometer 40, magnetometer 42, interface 52, and sensor interface circuitry 56.

Each of the pressure sensors 30, 32, 34, and 36 operates in association with the sensor interface circuitry 56 to produce, in response to the applied pressure force, a signal that is approximately proportional to the pressure force. Sensor calibration may be needed to assure that proportional response to the pressure force. Such calibration can be implemented in many different ways known to those skilled in the art. In the illustrated embodiment, if such calibration is needed, the microcontroller 46 is used to accomplish this calibration function.

The processor also includes a printed circuit board 60 that serves as a mounting surface that supports the other elements of the processor, namely, the wireless microcontroller 46, trigger 48, output device 50, interface 52, a power source 54, an analog conditioning and analog-to-digital converter circuit 56, and a multi-function communication bus 58 (i.e., I2C, RS232, and SPI). The printed circuit board 60 also serves as a mounting surface that supports the accelerometer 40 and the magnetometer 42. The total mass of the printed circuit board 60 and the elements supported by the printed circuit board 60 is estimated to be less than 20 grams. Further reduction in the size and mass likely is possible with miniaturization and integration.

The processor is substantially located within a housing 64 that is attached to the shoe 22. The housing 64 provides a port that facilitates the connection of the flex circuit 38 to the sensor interface circuitry 56. Additionally, the housing 64 has a port or ports that allow a wearer to actuate the trigger 48 and see the output device 50. A port is also provided in the housing that allows access to the interface 52.

The auxiliary device 26 is comprised of a microprocessor 70, memory 72, auxiliary device-tool interface 74, and auxiliary device-user interface 76. Generally, the microprocessor 70 receives data and/or information from the data acquisition and processing system 24 via the auxiliary device-tool interface 74, processes the data and/or information to generate energy efficiency related information for the wearer, and causes the energy efficiency related information to be provided to the wearer via the auxiliary device-user interface 76. The memory 72 stores the program or group of programs that are executed by the microprocessor 70. Further, in the illustrated embodiment, the memory 72 is capable of storing (1) data produced by the pressure sensors, accelerometer 40, and magnetometer 42, (2) feedback information derived from the data and determined pursuant to the operation of the microprocessor 70, and (3) information derived from the data and determined pursuant to the operation of the data acquisition and processing system 24 (to the extent such information has been transferred to the auxiliary device). The auxiliary device interface 74 operates in conjunction with the transceiver associated with the microcontroller 46 to facilitate communications between the auxiliary device 26 and the data acquisition and processing system 24 via a wireless channel. The wireless interface, in the illustrated embodiment, is a ZigBee interface but other wireless interfaces that convey information by electromagnetic signals are also feasible, such as an infra-red interface. In the illustrated embodiment, the interface 74 also includes a wired interface that allows the auxiliary device 26 to establish a wired communication channel with another device. The wired interface is a Universal Serial Bus (USB) interface. However, other wired interfaces are also feasible. Further, while the auxiliary device interface 74 and the data processing and acquisition system 24 each have a wireless and wired interface, only one interface is required. The wireless interface, however, provides the ability to communicate at any time when the auxiliary device 26 and the data acquisition and processing system 24 are within communication range. If the auxiliary device 26 is within range of the data acquisition and processing system 24 when data is being acquired by the sensors, the data can be downloaded from the system 24 to the auxiliary device 26. In contrast, the wired interfaces cannot practically be used for communications between the auxiliary device 26 and the system 24 when the sensors are being used to acquire data needed to generate feedback information for the wearer because a USB/RS232 converter cable extending between the interfaces will interfere with the use of the shoe 22 by the wearer. As such, the wire interfaces are typically used for communications between the auxiliary device 26 and the system 24 during periods of time when the sensors of the system 24 are not acquiring data and unlikely to acquire data for a meaningful period of time.

The auxiliary device-user interface 76 comprise an output device or peripheral that allows information resulting from the processing of the data by the auxiliary device 26 and/or information resulting from the processing of data provided by the microcontroller 46 to be provided to the wearer of the shoe 22 or person working with the wearer of the shoe to improve their performance. Preferably, the output device is a display screen, such an LCD display screen or comparable display screen. Other output devices and combinations of output devices are feasible. Among the possible other output peripherals are a printer and a speaker. The auxiliary device-user interface 76 also includes an input device that allows the user to communicate with the microprocessor 70. In one embodiment, the input device is a keyboard. However, other input peripherals or combinations of input peripherals are feasible. Among the possible other input peripherals that can be used in combination with the keyboard or as an alternative to the keyboard are a mouse, a trackball, a light pen, a microphone etc. It should be appreciated that, because the auxiliary device-user interface 76 includes an input device, the input device can be used in place of the trigger device 48 if the trigger device is broken or otherwise disabled, provided there is a communication channel established between the auxiliary device 26 and the system 24. Further, the input device can also be used to achieve much the same functions as the trigger 48 if a trigger 48 is not associated with the system 24, provided there is a communication channel established. Similarly, because the auxiliary device-user interface 76 includes an output device, the output device can be used in place of the output device 50 if the output device 50 is broken or otherwise disabled, provided there is a communication channel established between the auxiliary device 26 and the system 24. Further, the output device of the interface 76 can also be used to achieve much the same function as the output device 50 if the output device 50 is not associated with the system 24, provided there is a communication channel established.

The auxiliary device 26 preferably has dimensions and a weight that allows the device to be readily carried by an individual. For example, the device 26 can be in the form of a laptop computer, notebook computer, or hand-held computing device (such as a PDA) to name a few. The auxiliary device can also have dimensions and a weight that does not allow the device to be readily carried by an individual. However, when the auxiliary device 26 is implemented in this manner, the flexibility of the apparatus 20 is typically compromised.

The operation of the system 20 is now described when the wearer of the shoe is engaging in walking or running. Initially, the wearer places all of their weight on the foot with the shoe 22 and actuates the trigger 48 to cause the microcontroller 46 to read the data from the sensors 30, 32, 34, and 36 that reflect the weight of the wearer. In addition, the wireless communication link is established between the microcontroller 46 and the auxiliary device 26. After the link is established the data relating to the weight of the wearer is transferred to the auxiliary device 26. If a comparable shoe to shoe 22 is being worn on the other foot of the wearer, this initialization process is repeated for the comparable shoe. In many instances, the data derived from a single shoe will provide adequate information. However, data from two shoes will provide more refined and robust information. The following will describe the method of acquiring the data produced by a single shoe, the processing of this data to provide energy efficiency related feedback (i.e., energy efficiency, landing energy, and launching energy) and, if needed or desired, average power per step, average energy per step, average energy for a greater period of time than a single step (e.g., the entire exercise), and peak power. It should be understood that the same method would be applied to the data produced by the other shoe, if used.

Next, the wearer can begin walking or running and the microcontroller 46 will begin to acquire data from the sensors 30, 32, 34, and 36. The upper limit of the response frequency of the current sensors is about 100 Hz, which is greater than most all of the occurrences of the physical phenomena (e.g., the shoe 22 landing on the ground) being measured. While a lowering sampling rate could be used as know to those skilled in the art, the microcontroller 46 causes the sensors 30, 32, 34, and 36 to be sampled at about 500 Hz. This sampling rate provides higher quality data than if a lower sampling rate is utilized. The microcontroller 46, after receiving the data from the sensors 30, 32, 34, and 36, causes the data to be wirelessly transmitted to the auxiliary device 26 for analysis. If data from the accelerometer 40 and/or the magnetometer 42 is needed for some reason, this data is also wirelessly transmitted to the auxiliary device 26.

The following describes how the data from the four sensors 30, 32, 34, and 36 is analyzed to provide the energy efficiency related information and, to the extent needed or desired, information such average power and the like. It should be appreciate, however, that the process can be extended to any number of sensors and can be applied to as few as two sensors.

Nomenclature:

(1) Sensors 30, 32, 34 and 36 are represented as:

| A1 | A2 | A3 | A4 |
|---|---|---|---|

(2) The stationary full load signal sensor data, i.e., the data obtained at the time after the trigger 48 was actuated and when the wearer was placing their full weight on the shoe 22, are represented as:

| S1 | S2 | S3 | S4 |
|----|----|----|----|
| 3  | 2  | 2  | 1  |

To demonstrate the manner in which the stationary full load signal sensor data are used, a value for the signal or response produced by each of the sensors A1-A4 is provided. So, the response of sensor A1 (i.e., sensor 30) when the wearer put their entire weight on the shoe 22 is "3". Similarly, sensors A2, A3, and A4 respectively produced responses of "2", "2", and "1" at the same time as sensor A1 had a response of "3".

(3) Dynamic signal sensor data, i.e., the value of the signal or response from each of the sensors A1-A4 during a single sampling period during the landing phase, are represented as:

| D1 | D2 | D3 | D4 |
|----|----|----|----|
| 5  | 1  | 1  | 0  | values for a single sampling period during landing (D)

To demonstrate the manner in which the dynamic signal sensor data are used, a value for the signal or response produced by each of the sensors A1-A4 during a single sampling period during the landing phase is provided. So, the response of sensor A1 (i.e., sensor 30) during a single sampling period during the landing phase was "5". Similarly, sensors A2, A3, and A4 respectively produced responses of "1", "1", and "0" during the same sampling period as sensor A1 produced the response of "5".

(4) Dynamic signal sensor data, i.e., the value of the signal or response from each of the sensors A1-A4 during a single sampling period during the launching phase, are represented as:

| U1 | U2 | U3 | U4 |
|----|----|----|----|
| 0  | 5  | 4  | 2  | values for a single sampling period during launching (U)

To demonstrate the manner in which the dynamic signal sensor data are used, a value for the signal or response produced by each of the sensors A1-A4 during a single sampling period during the launching phase is provided. So, the response of sensor A1 (i.e., sensor 30) during a single sampling period during the launching phase was "0". Similarly, sensors A2, A3, and A4 respectively produced responses of "5", "4", and "2" during the same sampling period as sensor A1 produced the response of "0".

Energy Calculations (5) The Stationary Power Offset (SPO) (i.e., the power attributable to the weight of the wearer under stationary conditions) is calculated:

SPO=Sum of Squares of $S1$ to $S4$

SPO=$3^2+2^2+2^2+1^2$=18(for this example)

(6) The Dynamic Power Value (DPV), which is momentary sample power for landing and launching are represented as:

DPV$d$=$D1^2+D2^2+D3^2+D4^2$(for landing)

DPV$d$=$5^2+1^2+1^2+0^2$=27(for this example)

DPV$u$=$U1^2+U2^2+U3^2+U4^2$(for launching)

DPV$u$=$0^2+5^2+4^2+2^2$=45(for this example)

The need for differentiation between DPVd for landing and DPVu for launching will be explained later.

(7) Real Power (RP) and specifically RPd during landing and RPu during launching are calculated as follows:

RP$d$=DPV$d$–SPO

RP$d$=27–18=9(for this example)

RP$u$=DPV$u$–SPO

RP$u$=45–18=27(for this example)

The RPd represents the power associated with impact, i.e., during landing, and which is power lost. The RPu represents power delivered by athlete to propelling themselves forward.

(8) A single event out of a sequence of events needs to be taken into account. In the case of running, the single even is a single step. This is the point at which the distinction between landing and launching is explained. The span of time during which the shoe 22 is in contact with the ground has two distinct phases, landing and launching during running or walking. The landing phase starts at the moment when the shoe 22 begins to touch the ground or other surface and is identified by the sum of the squares of the signals output by the sensors A1-A4 (i.e., sensors 30, 32, 34, and 36) transitioning through a threshold value that is greater than the range of values associated with the noise output from the sensors A1-A4 calculated as a sum of squares when the sensors are under no load, i.e., when the shoe is in the air. The landing phase ends and the launching phase begins when the sum of the squares of the signals output by the sensors A1-A4 (i.e., sensors 30, 32, 34, and 36) is at a detectable minimum following the start of the landing phase and following the next maximum of the sum of the squares of the signals output by the sensors A1-A4. The end of the launching phase occurs when the sum of the squares of the signals output by the sensors A1-A4 (i.e., sensors 30, 32, 34, and 36) falls below the threshold value (see start of landing phase) following the start of the launching phase and following the next maximum of the sum of the squares of the outputs of the sensors A1-A4. The time when the sum of the squares of the outputs of the sensors A1-A4 (i.e., sensors 30, 32, 34, and 36) is below the threshold is when the shoe 22 is not in contact with the ground or other surface, i.e., in the air.

Figure 4A:
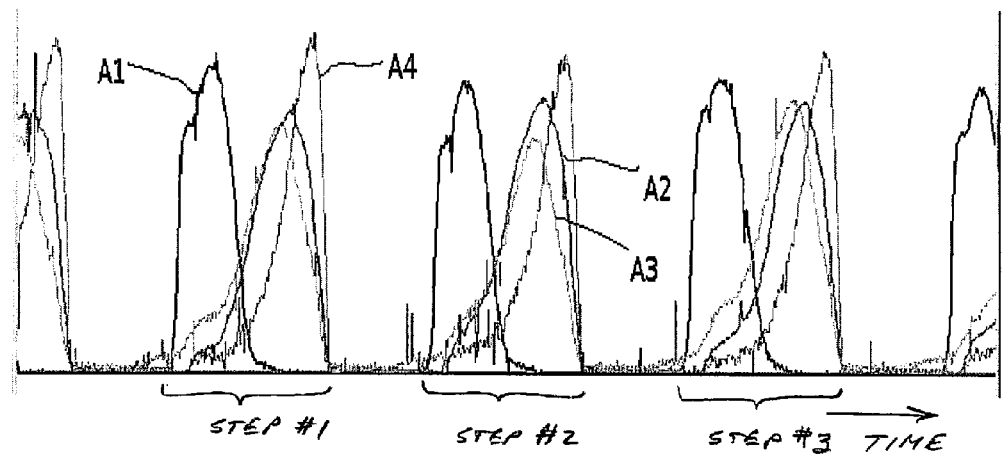
FIGS. 4A and 4B respectively illustrate the signals produced by the pressure sensors and the power curve generated based upon these pressure signals.
Figure 4B:
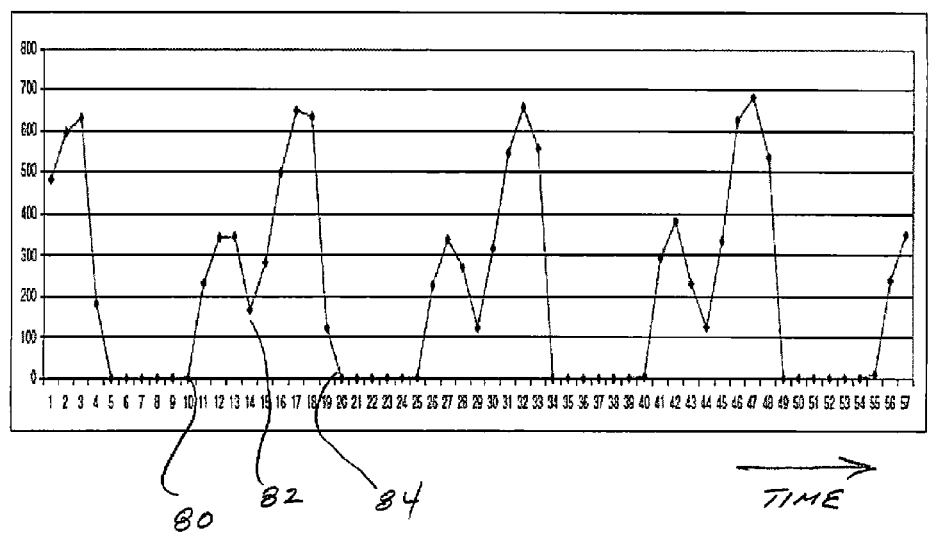

FIGS. 4A-4B are used to show the landing phase and launching phase associated with a step, the step being the time during which the shoe is in contact with the ground or other surface over which the wearer is moving. FIG. 4A illustrates the signals produced by sensors A1-A4 over several steps, each step starting with a substantial A1 signal (i.e., the signal produced by the heel pressure sensor 30) and ending with a substantial A4 signal (i.e., the signal produced by the toe pressure sensor 36). The time when the signals A1-A4 are very low is the time when the shoe 22 is in the air. FIG. 4B illustrates the power associated with each of the steps shown in FIG. 4A. The portion of the power plot in FIG. 4B that corresponds to one of the steps shown in FIG. 4A has a two-peak shape with the first peak being lower than the second peak. With respect to the two-peak curve that corresponds to step #1, the landing phase starts at point 80, the landing phase ends and the launching phase begins at point 82, and the launching phase ends at point 84. The area under the two-peak curve and between the times associated with points 80 and 82 represents energy being lost. The area under the two-peak curve and between the times associated with points 82 and 84 represents the energy delivered.

(9) With the periods of landing and launching determined, it is now possible to determine the energy lost during the landing period and the energy delivered during the launching period. The energy associated with the landing or launching is the integral of the real power (RP) over that period. In the case of landing, the energy lost is defined as Ed. Similarly, in the case of launching, the energy delivered is defined as Eu.

$$Ed = \text{Sum of } (RPd*T)$$

RPd represents the real power during a single sampling period associated with the landing phase; T is the duration of the sampling interval, and the sum is the sum of the products of RPd*T for each sample period associated with the landing phase.

$$Eu = \text{Sum of } (RPu*T)$$

RPu represents the real power during a single sampling period associated with the launching phase; T is the duration of the sampling interval, and the sum is the sum of the products of RPu*T for each sample period associated with the launching phase.

Eu should normally be greater than or equal to Ed.

(10) Since Ed is the energy that is being lost during landing and Eu is the energy that the athlete is delivering, the difference between Eu and Ed represent the useful energy associated with the desired motion (forward motion in the case of running or walking), Em, is defined as:

$$Em = Eu - Ed$$

(11) The energy efficiency (Ee) is the ratio between useful energy (Em) and launching energy (Eu).

$$Ee = (Eu - Ed)/Eu = Em/Eu$$

(12) Total useful energy TEm delivered by the athlete during exercise is equal to the sum of the Em's associated with each step over the exercise. Total energy delivered during the launching periods (TEu) is the sum of the Eu's associated with each step over the exercise. It should be appreciated that the athletes and their coaches may be interested in the average power and peak power delivered and average power and peak power converted into useful motion.

Average and Peak Power Calculation

(13) The average power delivered is the total launching energy (TEu) divided by the total time of the exercise.

(14) The average power converted into motion is TEm divided by the total time of the exercise.

(15) During certain types of exercise, the athlete may be required to deliver power over a relatively short period of time such that the delivered power is significantly greater than the average power being delivered by the athlete during the exercise. This greater power is termed peak power. The peak power is the maximum value of the average power delivered over a small number of steps where the number of steps is at least one step and significantly less than all of the steps taken during the exercise. This is a running calculation in which multiple sums of launching powers are calculated and compared to one another to determine the period of time and specific exercise phase during which peak power occurred.

The peak power converted into useful motion is calculated as a maximum of the average power converted into useful motion over the time associated with a small number of steps where the number of steps is at least one step and significantly less than all of the steps taken during the exercise. This is a running calculation in which multiple sums of powers converted into useful motion are calculated and compared to one another to determine the period of time and specific exercise phase during which peak of useful power occurred.

The foregoing description of the invention is intended to explain the best mode known of practicing the invention and to enable others skilled in the art to utilize the invention in various embodiments and with the various modifications required by their particular applications or uses of the invention.

What is claimed is:

1. A system for providing an athlete with energy related information comprising:
   a shoe with a plurality of pressure sensors located between the space to be occupied by a wearer's foot and the ground when the shoe is in use, each of the pressure sensors capable of producing an analog electrical signal indicative of the pressure being applied to the sensor;
   a processing system for processing the analog electrical signals output by the plurality of sensors to provide information related to the wearer's energy efficiency, the processing system comprising:
      analog-to-digital convertor for converting the analog electrical signals produced by the plurality of sensors into digital electrical signals at a predetermined sampling rate;
      a processor for processing the digital electrical signals to produce energy efficiency related information; and
      a display for providing a visual display of the energy efficiency related information;
      wherein the processor is adapted to process the digital signals to identify, with respect to a period of time during which the shoe is in contact with the ground or other surface, the start of the landing phase, the end of the landing phase and start of the launching phase, and the end of the launching phase.

2. A system, as claimed in claim 1, wherein the processor comprises:
   a first processor that is operatively attached to the shoe and adapted to receive the digital signals produced by the analog-to-digital converter and produce a wireless signal that includes the received digital signals; and
   a second processor that is spaced from the shoe and adapted to receive the wireless signal produced by the first processor.

3. A system, as claimed in claim 1, wherein the processor comprises:
   a first processor that is operatively attached to the shoe and adapted to receive the digital signals produced by the analog-to-digital converter, process the received digital signals to produce energy efficiency related information, and produce a wireless signal that includes the energy efficiency related information; and
   a second processor that is spaced from the shoe and adapted to receive the wireless signal produced by the first processor.

4. A system, as claimed in claim 1, wherein:

the processor is adapted to identify a portion of the digital signals that are associated with a stationary power offset of the sensors.

5. A system, as claimed in claim 4, wherein:

the processor is adapted to use the digital signals during each sampling period of the landing phase to determine a dynamic power value for each sampling period during the landing phase.

6. A system, as claimed in claim 5, wherein:

the processor is adapted to use the stationary power offset and the dynamic power value for each sampling period during the landing phase to determine the real power value for each sampling period during the landing phase.

7. A system, as claimed in claim 6, wherein:

the processor is adapted to integrate the real power value for each sampling period during the landing phase over the duration of the landing phase to determine energy lost during the landing phase.

8. A system, as claimed in claim 4, wherein:

the processor is adapted to use the digital signals during each sampling period of the launching phase to determine a dynamic power value for each sampling period during the launching phase.

9. A system, as claimed in claim 8, wherein:

the processor is adapted to use the stationary power offset and the dynamic power value for each sampling period during the launching phase to determine the real power value for each sampling period during the launching phase.

10. A system, as claimed in claim 9, wherein:

the processor is adapted to integrate the real power value for each sampling period during the launching phase over the duration of the launching phase to determine energy delivered during the launching phase.

11. A system, as claimed in claim 7 or 10, wherein:

the processor is adapted to use the energy delivered and the energy lost to determine one of: useful energy that contributes to the desired motion and energy efficiency.

* * * * *

UNITED STATES PATENT AND TRADEMARK OFFICE
CERTIFICATE OF CORRECTION

PATENT NO.         : 8,467,979 B2                                Page 1 of 1
APPLICATION NO.    : 12/901465
DATED              : June 18, 2013
INVENTOR(S)        : Zbigniew S. Sobolewski It is certified that error appears in the above-identified patent and that said Letters Patent is hereby corrected as shown below:

In the Specification:
At col. 3, line 48, delete "Jennie", and insert --Jennic--; and In the Claims:
At col. 12, claim 11, line 18, delete "the energy delivered and the energy lost", and insert --(a) the energy delivered as defined in claim 10 to determine one of: useful energy that contributes to the desired motion and energy efficiency or (b) the energy lost as defined in claim 7--.

Signed and Sealed this
Third Day of September, 2013

Teresa Stanek Rea
*Acting Director of the United States Patent and Trademark Office*